United States Patent [19]

Koehler et al.

[11] Patent Number: 5,543,515
[45] Date of Patent: Aug. 6, 1996

[54] PREPARATION OF TERTIARY AMINE OXIDES

[75] Inventors: Ulrich Koehler, Mannheim; Hardo Siegel, Speyer; Guenther Seybold, Neuhofen, all of Germany

[73] Assignee: BASF Aktiengesellschaft, Ludwigshafen, Germany

[21] Appl. No.: 285,756

[22] Filed: Aug. 3, 1994

Related U.S. Application Data

[63] Continuation of Ser. No. 983,228, Nov. 30, 1992, abandoned.

[30] Foreign Application Priority Data

Dec. 6, 1991 [DE] Germany .......................... 41 40 259.6

[51] Int. Cl.⁶ .................... C07C 209/00; C07D 223/02; C07D 295/24
[52] U.S. Cl. .................... 540/604; 544/173; 544/383; 546/133; 546/184; 548/542; 546/298
[58] Field of Search ................ 540/604; 544/173, 544/383; 546/133, 184; 548/542; 564/298

[56] References Cited

U.S. PATENT DOCUMENTS

| | | | |
|---|---|---|---|
| 3,447,939 | 6/1969 | Johnson | 106/135 |
| 4,014,933 | 3/1977 | Boettger et al. | 260/563 |
| 4,218,391 | 8/1980 | Romano et al. | 260/463 |
| 4,247,480 | 1/1981 | Murata et al. | 564/298 |
| 4,748,241 | 5/1988 | Scholten et al. | 544/173 |
| 5,002,922 | 3/1991 | Irgang et al. | 502/331 |
| 5,023,376 | 6/1991 | Shehad et al. | 540/474 |
| 5,223,644 | 6/1993 | Blezard et al. | 564/298 |

FOREIGN PATENT DOCUMENTS

| | | |
|---|---|---|
| 0307184 | 3/1989 | European Pat. Off. . |
| 0320694 | 6/1989 | European Pat. Off. . |
| 0356918 | 3/1990 | European Pat. Off. . |
| 413259 | 2/1991 | European Pat. Off. . |
| 0426084 | 5/1991 | European Pat. Off. . |
| 2632638 | 12/1989 | France . |
| 1953263 | 2/1972 | Germany . |
| 1694048 | 3/1972 | Germany . |
| 2743690 | 1/1980 | Germany . |
| 3618352 | 12/1987 | Germany . |

OTHER PUBLICATIONS

Kaczmarek, Chemical Abstract 117:131022r (1992).
R. Schroeter, Houben–Weyl, Methoden der Organischen Chemie, pp. 1029–1033 (1955).
Organic Syntheses, 58, pp. 43–53, 1978, "Catalytic Osmium Tetroxide Oxidation . . . ".
T. Greene, "Protective Groups in Organic Synthesis", pp. 223–287, 1981, Wiley Intsci.
Chem. Rev., 64, pp. 645–649, 1964, Matzner et al., "The Chemistry of Chloroformates".
J. Gen. Chem. (USSR), 17, pp. 2256–2258, 1947.
Organikum; 17 Ed.; pp. 402–408, 419–424; 170–177; 307–313; 545–547; 557–561 (1988).
Weissermel, Arpe, Industrielle Organische Chemie, pp. 343–349, 359–365; Verlag Chemie, Weinheim 1978.
J. Org. Chem., 27, 1901 (1962), "An Improved Synthesis of Dicarbonates . . . ", Howe and Morris.
Houben–Weyl, vol. E1; pp. 245–252; 273–286; 313–322 (1982).
Houbel–Weyl, vol. E2; pp. 150–165; 315–338; 487–498 (1982).
Analytical Chemistry, vol. 51, No. 11, 1979, Krull et al., "Confirmatory methods for the Thermal Energy Determination of N–Notroso Compounds at Trace Levels".

*Primary Examiner*—Philip I. Datlow
*Attorney, Agent, or Firm*—Keil & Weinkauf

[57] ABSTRACT

A process for preparing tertiary amine oxides with a low nitrosamine content by reacting a tertiary amine with an aqueous solution of hydrogen peroxide, which comprises using as starting material tertiary amines whose total content of primary and secondary amines is not more than 0.05% by weight.

18 Claims, No Drawings

PREPARATION OF TERTIARY AMINE OXIDES

This application is a continuation of application Ser. No. 07/983,228, filed on Nov. 30, 1992, now abandoned.

The present invention relates to a process for preparing tertiary amine oxides with a low nitrosamine content by reacting a tertiary amine with an aqueous solution of hydrogen peroxide.

Tertiary amine oxides can be prepared by the process of DE-A 16 94 048 in which the relevant tertiary amines are reacted with an aqueous solution of hydrogen peroxide, and they are used, for example, as solvents for cellulose, polyamides and potypeptides in fiber production. Furthermore, tertiary amine oxides are used as cooxidants for the preparation of vicinal diols from olefins using osmium tetroxide (cf. Org. Synth. 58 (1978) 43). Particularly important for the said uses is N-methylmorpholine N-oxide. Since tertiary amine oxides have only moderate storage stability and tend as the pure substances to eliminate oxygen, they are normally stored and marketed in the form of their solutions, generally in the form of their aqueous solutions. For example, N-methylmorpholine N-oxide is usually marketed as a 50–60% by weight aqueous solution.

One problem of the use of tertiary amine oxides is their contamination with nitrosamines which are regarded as carcinogens. There has therefore been no lack of attempts to develop processes for preparing tertiary amine oxides with a low nitrosamine content. FR-A 26 32638 describes the inhibiting effect of carbon dioxide on nitrosamine formation in the preparation of tertiary amine oxides, but EP-A 320 694 states that addition of carbon dioxide on its own is not sufficient for satisfactory reduction of nitrosamine formation and therefore the reducing agent ascorbic acid must also be added to the reaction mixture. According to EP-A 356 918, the preparation of tertiary amine oxides in the presence of carbon dioxide and metallic titanium results in tertiary amine oxides with a reduced nitrosamine content. The two latter processes have the disadvantage that, on the one hand, a costly auxiliary, ascorbic acid, must be added to the reaction mixture and cannot be recovered and, on the other hand, the use of metallic titanium to reduce the nitrosamine content means that the process has to be more technically elaborate on the industrial scale. This makes both processes considerably more costly.

U.S. Pat No. 4,247,480 discloses the preparation of tertiary amine oxides by oxidizing tertiary amines with hydrogen peroxide in the presence of carbon dioxide and chelating agents such as diethylenetriaminepentaacetic acid, polyphosphoric acids and polycarboxylic acids, the chelating agents being intended to prevent decomposition of the hydrogen peroxide by traces of heavy metals.

EP-A 307 184 proposes reducing the reaction temperature in order to reduce the nitrosamine formation in the preparation of tertiary amine oxides in the presence of carbon dioxide. The decrease in the reaction rate associated with this reduction in temperature makes this process uneconomic because of the low space-time yields. Furthermore, there is a risk in this process of dangerous accumulation of hydrogen peroxide in the reactor.

According to EP-A 426 084, the use of carbon dioxide also results in discoloration of the tertiary amine oxide product, which is said to be remedied by working under an inert gas atmosphere, which in turn makes the process costly.

It is an object of the present invention to provide a simple and economic process for preparing tertiary amine oxides with a low nitrosamine content.

We have found that this object is achieved by the process in which a tertiary amine is reacted with an aqueous solution of hydrogen peroxide, which comprises using as starting material tertiary amines whose total content of primary and secondary amines is not more than 0.05% by weight.

Tertiary amines containing less than 0.05% by weight, preferably less than 0.02% by weight, of primary and secondary amines can be obtained, for example, by distillation from the relevant tertiary amines which have a content of these primary and secondary amines derived from the preparation. In order to reduce the possibly great expense of such a distillation, it is expedient to add to the contaminated tertiary amines scavengers which selectively react with the primary and secondary amines. The compounds formed in this way can remain in the tertiary amine treated in this way without interfering with the subsequent generation of the tertiary amine oxide with a peroxide, in particular hydrogen peroxide. It is possible if required to remove these scavengers and their derivatives which are formed on reaction with the primary and/or secondary amines from the tertiary amine by distillation, extraction, filtration or centrifugation.

The scavengers which can be used for this purpose are in principle substances which react faster with primary and secondary amines than with tertiary amines and whose reaction with these amines takes place as completely as possible after the minimum time. Thus the reagents which can be employed particularly advantageously as scavengers for primary and secondary amines are all those which are used in organic synthetic chemistry for protection, ie. blocking the amine group, in the synthesis of organic molecules. Reagents for introducing protective groups onto primary and/or secondary amines are described by T. Greene in Protective Groups in Organic Synthesis, 223–287, Wiley Interscience, New York 1981.

Examples of reagents which can be employed for removing primary and secondary amines from tertiary amines belong to the following classes of compounds: haloformates, haloformamides, carboxylic anhydrides, acyl halides, carboxylic esters, ketenes and their dimers, phosgene, carbonic esters, pyrocarbonic esters, isocyanates, phosphinyl halides, phosphonyl halides, phosphoryl halides, sulfenyl halides, sulfonyl halides, sulfonic esters or anhydrides.

are employed to trap the primary and/or secondary amines there is formation of the relevant carbamic esters IIa

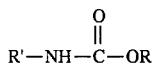

and/or IIb

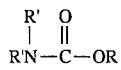

which can easily be separated by distillation from the tertiary amine which does not react with these reagents. It is possible in principle to use all types of haloformates, ie. those in which Hal is fluorine, chlorine, bromine or iodine, and R can be a suitable aliphatic or aromatic radical, but because they are easy to prepare and, in particular, for reasons of cost alkyl chloroformates are preferably used, particularly preferably $C_1$–$C_4$-alkyl chloroformates. These compounds can be prepared in a straightforward manner by reacting phosgene with the relevant alcohols, for example as described by Matzner et al., Chem. Rev. 64 (1964) 645.

It is also possible in place of the haloformates to use haloformamides of the formula III

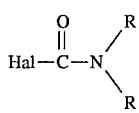

to trap amines. Reaction of the haloformamides with primary and secondary amines results in the corresponding ureas of the formula IVa

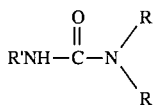

and IVb

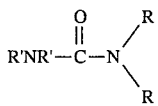

from which the tertiary amine can be straightforwardly removed by distillation. Just as for the haloformates, it is possible in principle to use all haloformamides for this reaction, but because they are easy to prepare and are available at reasonable cost chlorodialkylformamides, especially chloro-di-$C_1$-$C_4$-alkylformamides are preferred. These chlorodialkylformamides can be obtained by the generally applicable process of Rudenko et al., J. Gen. Chem. (USSR) 17 (1947) 2256 (Chemical Abstracts 47, 4918) by reacting phosgene with dialkylamines.

Carboxylic anhydrides react with the primary and secondary amines to form the relevant carboxamides from which the tertiary amine can easily be removed by distillation. It is possible in principle to use every carboxylic anhydride to remove unwanted amines from the tertiary amine, but phthalic anhydride and the open-chain or cyclic anhydrides of $C_2$-$C_4$-mono- and/or dicarboxylic acids, namely acetic anhydride, propionic anhydride, maleic anhydride and succinic anhydride, are particularly preferably used.

Just like the carboxylic anhydrides, the acyl halides form carboxamides on reaction with primary and secondary amines. In this case too it is possible in general to use all acyl halides for acylating the primary and secondary amines, but for economic reasons the halides of simple, low-cost carboxylic acids are preferred, especially $C_2$-$C_4$-acyl halides such as acetyl, propionyl and butyryl halides, and benzoyl and phthaloyl halides. It is possible to use acyl fluorides, chlorides, bromides and iodides, but acyl chlorides are expediently used for reasons of cost.

Carboxylic esters can also be used for the acylation of the primary and secondary amines. In principle there is no restriction on the carboxylic ester used in this acylation method either. Preferred carboxylic esters are, for reasons of cost, the esters of benzoic acid and phthalic acid and the esters of $C_1$-$C_6$-mono- and dicarboxylic acids, especially the esters of formic acid, acetic acid, propionic acid, maleic acid, succinic acid and adipic acid. It is, of course, also possible to use internal esters of carboxylic acids, ie. lactones, for acylating the primary and secondary amines. A preferred lactone for this purpose is γ-butyrolactone.

The carboxylic esters and anhydrides and acyl halides can be prepared by the standard methods in Organikum, Organisch-chemisches Grundpraktikum, 17th edition, 402–408 and 419–424. Maleic anhydride and phthalic anhydride are basic chemicals and are produced on the industrial scale, for example by the partial oxidation of butane or butene and xylene, respectively, by the processes described by Weissermel, Arpe in Industrielle Organische Chemie, 343–349 and 359–365, Verlag Chemie, Weinheim 1978. Hydrogenation of the double bond in maleic anhydride results in succinic anhydride, and further hydrogenation results in γ-butyrolactone.

The primary and secondary amines can also be advantageously converted into easily removable carboxamides using the ketenes of the formula V

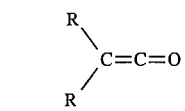

where the R radicals can be identical or different and can be hydrogen, aryl, especially phenyl, and/or $C_1$-$C_{20}$-alkyl, or the cyclic dimers thereof of the formula VI

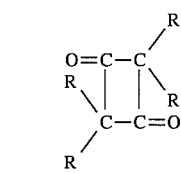

The ketenes can be generated, for example, from the corresponding carboxy acids by elimination of water or from the corresponding acyl halides by elimination of hydrogen halide, for example by the methods of J. March, Advanced Organic Chemistry, 3rd edition, 902+916, Wiley, New York 1985. All of them are very reactive and spontaneously add onto primary and secondary amines to form amides. Particularly preferably used is ketene Va $$H_2C=C=O \qquad \text{Va}$$

which can be obtained from acetic acid, and its cyclic dimer.

Phosgene and its sulfur analog, thiophosgene, are also suitable, because of their higher reactivity, for trapping the primary and secondary amines, in which case involatile urea and thiourea derivatives are formed, from which the tertiary amine can easily be removed by distillation.

Carbonic esters of the formula VII

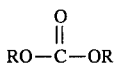

and pyrocarbonic esters of the formula VIII

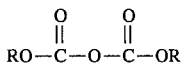

react with the primary and secondary amines to give carbamic esters IIa and IIb respectively. In this case too it is possible in principle to use all carbonic and pyrocarbonic esters, but the low-cost phenyl, benzyl and $C_1$-$C_6$-alkyl derivatives are preferably used. The carbonic esters VII can be obtained, for example, by the process of DE-A 27 43 690, and pyrocarbonic esters can be obtained, for example, by the process of Howe et al., J. Org. Chem. 27 (1962) 1901. It is also, of course, possible to use cyclic carbonic esters such as propylene carbonate to trap the primary and secondary amines.

Involatile ureas are formed on reaction of the primary and secondary amines with isocyanates IX $$R-N=C=O \qquad \text{IX}$$

in which case it is expedient to use the low-cost isocyanates which are employed as intermediates in the preparation of crop protection agents or as monomers in the preparation of polyurethanes and polyureas. Representatives of such isocyanates which may be mentioned are toluylene diisocyanate, hexamethylene diisocyanate, 4,4'-methylenedi(phenyl isocyanate), isophorone diisocyanate, $C_1$–$C_6$-alkyl isocyanates, phenyl isocyanate and tolyl isocyanate.

Also suitable as scavengers for primary and secondary amines are phosphinous halides of the formula Xa

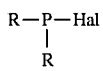   Xa and phosphinyl halides of the formula Xb

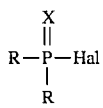   Xb

Phosphonous dihalides and phosphonous ester halides of the formula XI

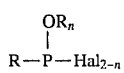   XI where n is 0 or 1, phosphonyl halides of the formula XII

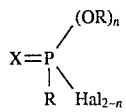   XII where n has the abovementioned meaning, and phosphorous ester halides of the formula XIII

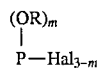   XIII where m is 0, 1 or 2, and phosphoryl halides of the formula XIV

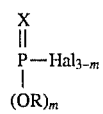   XIV where m has the abovementioned meaning. X in these phosphorus-containing scavengers can be sulfur or, preferably, oxygen. The R radicals can have any chosen meaning but, because of their low cost, preferred scavengers are those in which R is $C_1$–$C_6$-alkyl or phenyl. The halogens in the phosphorus-containing scavengers can also be chosen freely but the relevant chlorine compounds will usually be preferably employed. Phosphinous halides Xa and phosphinyl halides Xb can be obtained by the processes described in Houben-Weyl, Methoden der Organischen Chemie, Volume E1, 245 et seq., Thieme, Stuttgart 1982 and Volume E2, 150 et seq., Thieme, Stuttgart 1982, and phosphonous ester halides XI can be obtained by the process of Houben-Weyl, Volume E1, 273 et seq. Phosphonyl halides XII can be prepared as described in Houben-Weyl, Volume E2, 315 et seq., and phosphorous ester halides XIII can be prepared by the process of Houben-Weyl, Volume E1, 313 et seq. Phosphoryl halides XIV can be obtained by the process of Houben-Weyl, Volume E2, 487 et seq. All these phosphorus-containing halogen compounds react with the primary and secondary amines to give the corresponding amides.

Further reagents which can advantageously be used for the selective derivatization of primary and secondary amines are sulfonyl halides of the formula XV

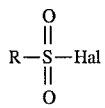   XV which form involatile sulfonamides on reaction with the latter. Hal in the sulfonyl halides can be fluorine, chlorine or bromine, and sulfonyl chlorides are preferably used. The sulfonyl halides which are expediently used as scavengers are those which are commercially available at low cost, especially methanesulfonyl chloride, ethanesulfonyl chloride, benzenesulfonyl chloride, toluenesulfonyl chloride and naphthalenesulfonyl chloride. It is also possible in place of the sulfonyl halides to use the esters, especially the $C_1$–$C_6$-alkyl and phenyl esters, of the sulfonic acid for trapping the primary and secondary amines present in the tertiary amine. Sulfonyl chlorides and sulfonic esters of these types can be prepared, for example, by the methods in Organikum, Organisch-chemisches Grundpraktikum, 17th edition, 170–171, 307–313, 545–547 and 557–561, VEB Deutscher Verlag der Wissenschaften, Berlin 1988.

It is also possible to use in the same way as the sulfonyl halides the sulfenyl halides of the formula XVI

   XVI or sulfinyl halides of the formula XVII

   XVII but these are generally not so preferred because they are usually more costly.

If the tertiary a mines used as starting materials for preparing tertiary amine oxides according to the invention have a content of primary and secondary amines which has been reduced by the said treatment process to less than 0.05% by weight, preferably to less than 0.02% by weight, there is a drastic reduction in the nitrosamine content of the tertiary amine oxides prepared in this way.

In the particularly preferred embodiment of the process according to the invention, the tertiary amines used as starting materials for preparing the tertiary amine oxides are not separated from the primary and secondary amines present therein by one of the treatment methods described in a separate stage; on the contrary the scavengers for the primary and secondary amines are added to the mixture for the conversion of the tertiary amines into the tertiary amine oxides and incubated with the tertiary amines before addition of the oxidizing agent. Essentially nitrosamine-free tertiary amine oxides are obtained in this embodiment of the process according to the invention.

It is possible to use all the abovementioned scavengers for primary and secondary amines in this preferred embodiment of the process according to the invention. However, it is particularly preferable to use in this process variant carbonyl halides, especially $C_1$–$C_4$-carbonyl halides and benzoyl halides, preferably the chlorides, carboxylic anhydrides, especially $C_2$–$C_4$-car-boxylic anhydrides and phthalic anhydride, ketenes and their dimers, especially $C_2$–$C_4$-ketenes and their dimers, sulfonyl halides, especially $C_1$–$C_4$-sulfonyl halides and aromatic sulfonyl halides such as benzenesulfonyl halides and toluenesulfonyl halides, preferably the chlorides, and phosphoryl halides, especially phosphoryl chlorides. Particularly preferred scavengers are acetyl chloride, acetic anhydride, ketene, phthalic anhydride, maleic and succinic anhydrides, methanesulfonyl chloride, benzenesulfonyl chloride, toluenesulfonyl chloride, dimethoxyphosphoryl chloride and phosphoryl chloride.

These scavengers can be used in stoichiometric amounts relative to the primary and secondary amines present in the tertiary amine, but they are expediently added in excess relative to the amines to be removed. In general, from 1.1 to 10 times, preferably from 1.5 to 3 times, the stoichiometric amount of the scavenger is added to remove the primary and secondary amines. These amounts apply both to the variant in which the primary and secondary amines are removed in a separate stage and to the embodiment in which the unwanted amines are trapped in the vessel for the preparation of the amine oxide before addition of the oxidizing agent. It is also possible, of course, to add larger excesses of scavenger. The amount of scavenger to be added can easily be determined by measuring the content of the various primary and secondary amines in the tertiary amine starting material by gas chromatography in a conventional manner.

Before they are oxidized to the amine oxides, the tertiary amines are usually incubated with the scavengers for from 0.25 to 3 h, preferably 0.5 to 2 h, and particularly preferably from 1 to 1.5 h, and from 0° to 150° C., preferably 20° to 80° C., and particularly preferably at room temperature. The incubation can be carried out under atmospheric pressure or under elevated pressure, especially the autogenous pressure of the reaction system, preferably under atmospheric pressure. It is possible with particularly reactive scavengers, such as ketenes or acid chlorides, and when elevated temperatures are used, to reduce the incubation time necessary for maximum derivatization of the unwanted a mines, but it may be more expedient for economic reasons to incubate at lower temperatures and for longer times.

The incubation with the scavenger used for derivatization of the primary and secondary a mines can be followed by addition to the reaction mixture, without working up, of the oxidizing agent to convert the tertiary a mines into tertiary amine oxides. The oxidation of the tertiary a mines to the corresponding amine oxides can be carried out with the oxidizing agents customary for this purpose, but as a rule an aqueous solution of hydrogen peroxide is used, and examples of oxidation processes which can be used are those of DE-A 36 18 352 and DE-A 16 94 048. The reaction product can also be worked up by conventional methods, for example those in the abovementioned publications.

The process according to the invention can in principle be used for the preparation of all tertiary amine oxides from tertiary amines. The process according to the invention is particularly suitable for preparing tertiary amine oxides from tertiary aliphatic amines of the formula XVIII

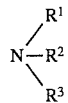
XVIII where $R^1$, $R^2$ and $R^3$ can be identical or different and can be $C_1$–$C_{20}$-alkyl, preferably $C_1$–$C_{10}$-alkyl and particularly preferably $C_1$–$C_6$-alkyl, $C_3$–$C_8$-cycloalkyl, preferably $C_5$–$C_6$cycloalkyl, $C_7$–$C_{12}$-aralkyl, preferably benzyl, and unsubstituted or substituted phenyl or naphthyl, and where, alternatively, $R^1$ and $R^2$ can be linked together to give a 3- to 10-membered cycloaliphatic ring which can also contain an oxygen as hetero atom. Particularly preferred cycloaliphatic tertiary amines are those where $R^1$ and $R^2$ form together with the nitrogen a 5- to 7-membered cycloaliphatic ring, and $R^3$ is $C_1$–$C_{10}$-alkyl, preferably $C_1$–$C_4$-alkyl. The examples of particularly preferred starting compounds of this type are N-methylpyrrolidine, N-ethylpyrrolidine, N-n-propylpyrrolidine, N-n-butylpyrrolidine, N-methylpiperidine, N-ethylpiperidine, N-n-propylpiperidine, N-n-butylpiperidine, N-methylmorpholine, N-ethylmorpholine, N-n-propylmorpholine, N-n-butylmorpholine and N-methylazacycloheptane. Other tertiary amines which can advantageously be used as starting material for preparing tertiary amine oxides by the process according to the invention are N,N'—$C_1$–$C_4$-dialkylpiperazines and quinuclidine. Said tertiary amines are commercially available or can be prepared from the corresponding alcohols by reductive amination with ammonia, eg. by the processes of DE-A 19 53 263 and U.S. Pat. No. 5,002,922.

Using the process according to the invention it is possible with minimal effort to obtain solutions of tertiary amine oxides whose nitrosamine content is below 20 ppb, determined by coupled gas chromatography/mass spectrometry or by the method of Krull et al., Anal. Chem. 51 (1979) 1706.

EXAMPLES

Comparative example

Preparation of N-methylmorpholine N-oxide (NMO) from N-methylmorpholine (NMM) containing 0.3% by weight of primary and secondary amines.

101 g of NMM (1.0 mol) were introduced into a 500 ml stirred apparatus under a nitrogen atmosphere and, while stirring, 102.4 g of hydrogen peroxide in the form of a 30% by weight aqueous solution (0.9 mol) were added at 70° C. over the course of 2 h. After the hydrogen peroxide addition was complete,the mixture was stirred at this temperature for a further 7 h. About 20 ml of excess aqueous NMM were then removed by distillation at 60° C. under 100 mbar. The distillation residue was an approximately 57% by weight aqueous solution of NMO. Analytical data on the resulting NMO solution: residual NMM content: <0.1% by weight nitrosamine content: 3100 ppb The NMM and NMO content in the NMO solution was determined by acid-based titration with potentiometric detection, and its nitrosamine content was measured by gas chromatography/mass spectrometry after previous removal of the NMM and NMO on an acid ion exchanger. These analytical methods were used for all the NMO samples.

Example 1

(according to the invention)

An approximately 57% by weight aqueous solution of NMO was prepared by the process of the comparative example from NMM whose content of primary and secondary amines had been reduced by distillation to 0.02% by weight.

Analytical data:

residual NMM content: <0.1% by weight nitrosamine content: <50 ppb

Example 2

101 g of NMM which had a content of 0.3% by weight of primary and secondary amines was stirred with 0.65 g (4.5 mmol) of acetic anhydride at room temperature for 1 h and then oxidized to NMO and worked up as described in the comparative example.

The resulting 57% by weight NMO solution had the following analytical data:

residual NMM content: <0.1% by weight nitrosamine content: <20 ppb

In further experiments using this process, the acetic anhydride was replaced as scavenger by in each case 4.5 mmol of p-toluenesulfonyl chloride, acetyl chloride, gaseous ketene, methanesulfonyl chloride and dimethoxyphosphoryl chloride of the formula XIX

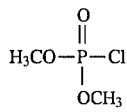 XIX

The residual NMM content was in each case <0.1% by weight, while the nitrosamine content was less than 20 ppb in all the NMO solutions prepared in this way.

We claim:

1. In a process for producing tertiary amine oxides by reacting a tertiary amine with hydrogen peroxide, the improvement which comprises, adding to a solution containing tertiary amines, primary amines and secondary amines a scavenger for primary and secondary amines in an amount sufficient to reduce the content of primary and secondary amines to less than 0.05% by weight, and thereafter reacting the tertiary amines with hydrogen peroxide to form tertiary amine oxides having a drastically reduced nitrosamine content.

2. A process as claimed in claim 1, wherein the scavenger is from the class of acyl halides, carboxylic anhydrides, ketenes, sulfonyl halides or phosphoryl halides.

3. A process as defined in claim 1 wherein the scavenger is selected from the group consisting of haloformates, haloformamides, carboxylic anhydrides, acyl halides, carboxylic esters, ketenes and their dimers, phosgene, carbonic esters, pyrocarbonic esters, isocyanates, phosphinyl halides, phosphoryl halides, sulfenylhalides, sulfonyl halides, and sulfonic esters or anhydrides.

4. The process of claim 3, wherein the scavenger is a haloformate.

5. The process of claim 3, wherein the scavenger is a haloformamide.

6. The process of claim 3, wherein the scavenger is a carboxylic anhydride.

7. The process of claim 3, wherein the scavenger is an acyl halide.

8. The process of claim 3, wherein the scavenger is a carboxylic ester.

9. The process of claim 3, wherein the scavenger is a ketene and its dimers.

10. The process of claim 3, wherein the scavenger is a phosgene.

11. The process of claim 3, wherein the scavenger is a carbonic ester.

12. The process of claim 3, wherein the scavenger is a pyrocarbonic ester.

13. The process of claim 3, wherein the scavenger is an isocyanate.

14. The process of claim 3, wherein the scavenger is a phosphinyl halide.

15. The process of claim 3, wherein the scavenger is a phosphoryl halide.

16. The process of claim 3, wherein the scavenger is a sulfenyl halide.

17. The process of claim 3, wherein the scavenger is a sulfonyl halide.

18. The process of claim 3, wherein the scavenger is a sulfonic ester or anhydride.

* * * * *